United States Patent [19]

Fallis et al.

[11] 4,104,286

[45] Aug. 1, 1978

[54] CHOLESTEROL SEPARATION PROCESS

[76] Inventors: Alexander Graham Fallis, 22 Laurier St., St. John's, Newfoundland, Canada, A1A 2W3; John Marshall William Scott, 34 Poplar Ave., St. John's, Newfoundland, Canada; June Gertrude Winter, 4 Yellowknife St., St. John's, Newfoundland, Canada, A1A 2Z8

[21] Appl. No.: 759,443

[22] Filed: Jan. 14, 1977

[30] Foreign Application Priority Data

Nov. 19, 1976 [CA] Canada .................................. 266152

[51] Int. Cl.² ............................................. C07J 9/00
[52] U.S. Cl. ............................................. 260/397.25
[58] Field of Search ................................... 260/397.25

[56] References Cited

U.S. PATENT DOCUMENTS

| 2,753,362 | 7/1956 | Owades et al. ............... 260/397.25 |
| 3,332,969 | 7/1967 | Hutt, Jr. et al. ............... 260/397.25 |

*Primary Examiner*—Elbert L. Roberts
*Attorney, Agent, or Firm*—Murray & Whisenhunt

[57] ABSTRACT

A process is provided for isolating the crystalline chemical compound, cholesterol, from dried whole egg and dried egg yolk obtained from domestic hen eggs. This process provides not only free cholesterol, but also edible whole egg that is reduced in cholesterol and edible egg yolk powder that is reduced in cholesterol. The process includes extraction with aqueous ethanol, saponification in aqueous ethanolic alkali metal hydroxide, and concentration and purification with a hydrocarbon solvent and methanol. The products obtained include free cholesterol, essentially cholesterol-free edible egg powder, i.e., either whole egg or egg yolk, and saponified fats, recovered in the form of their salts.

11 Claims, 1 Drawing Figure

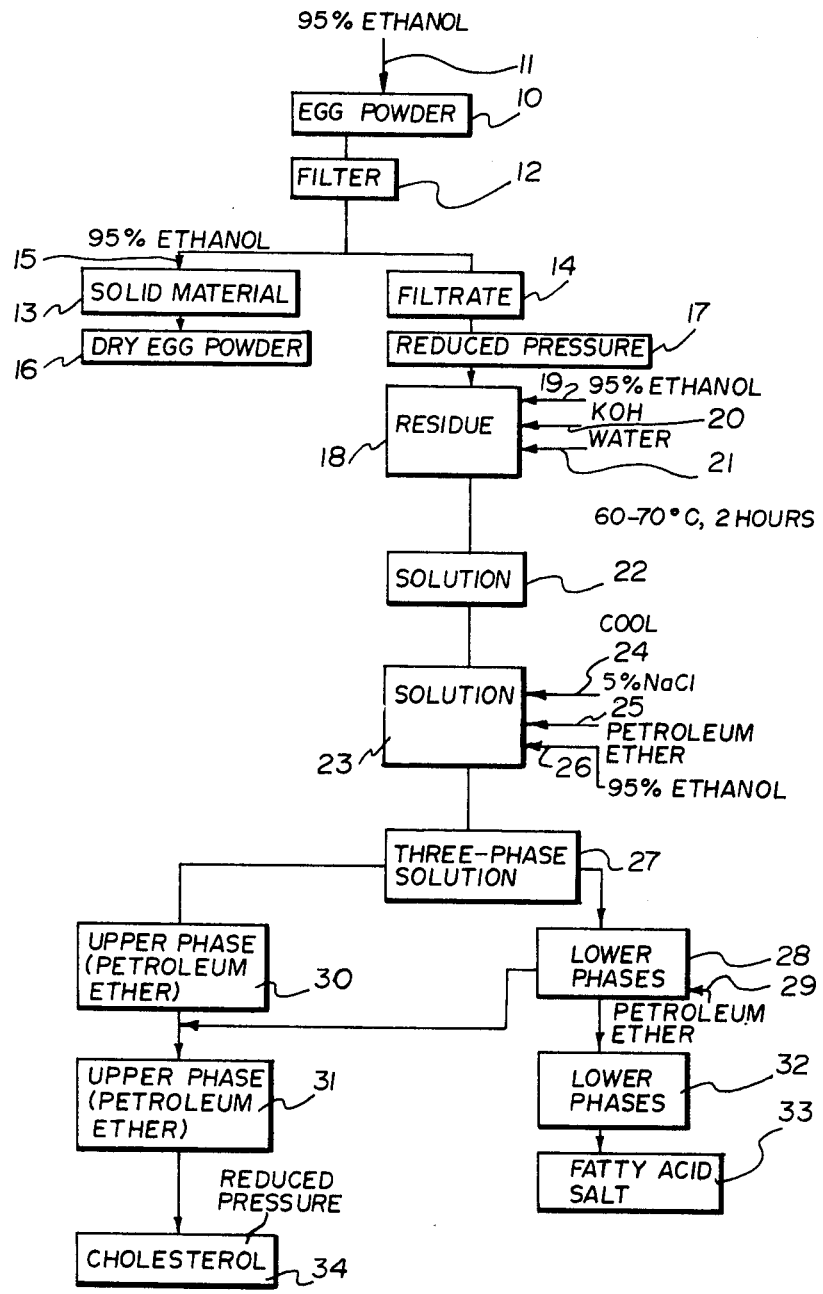

CHOLESTEROL SEPARATION PROCESS

BACKGROUND OF THE INVENTION

(i) Field of the Invention

This invention relates to a process for isolating cholesterol from eggs. In particular, this invention relates to a process for isolating cholesterol from dried whole egg or from dried egg yolk obtained from domestic hen eggs, thus providing not only free cholesterol, but also providing edible whole egg that is reduced in cholesterol or edible egg yolk powder that is reduced in cholesterol.

(ii) Description of the Prior Art

Cholesterol is a suitable precursor in recently developed routes to chemical substances used for oral birth control, as well as in routes to substances that can be used for production of Vitamin D, and in the manufacture of derivatives which are used in liquid crystal devices. Consequently, many procedures have been developed for isolating cholesterol from materials containing cholesterol. Most of these methods heretofore used merely relied on the use of a solvent to extract the cholesterol from the raw material under specified conditions. For example, U.S. Pat. No. 2,371,467 to Porsche describes a process for isolating cholesterol from animal nerve tissue by extracting cholesterol from the tissue with ethylene dichloride. Thus, many of the above-described procedures produced crude, rather than substantially pure, cholesterol. Canadian Pat. No. 498,384 issued Dec. 15, 1953 to Armour & Co. purported to be an improvement on those procedures by providing a process for treating crude cholesterol by dissolving the cholesterol in an alkali metal hydroxide solution containing 85% alcohol, then crystallizing cholesterol from solution, and finally washing the crystallized cholesterol.

However, this procedure suffers the deficiency that it is generally not utilizable to provide cholesterol directly from the raw cholesterol-containing material, and the by-products from which the cholesterol has been removed are generally not useful.

Eggs from domestic hens (hereafter referred to as eggs) are constituted of water, protein, fat (including cholesterol), carbohydrate, minerals, and vitamins. The average representative compositions of these materials in eggs is tabulated below in Table I.

TABLE I

| Constituent | Approximate Composition (g per 100 g of whole raw egg) |
|---|---|
| water | 74 |
| protein | 13 |
| fat | 11 |
| (cholesterol) | (0.76) |
| carbohydrate | 0.7 |
| minerals | 1 |
| vitamins | |

It has long been recognized that eggs are a most desirable food in contributing to the nutritional requirements of man. Unfortunately, as pointed out above, the yolk of egg is one of the richest sources of dietary cholesterol. Cholesterol from egg yolk-containing foods contributes increased serum cholesterol levels that are often associated with heart and circulatory diseases. In addition egg fat possesses a low ratio of polyunsaturated to saturated fatty acids. In the past years emphasis has been placed on the desirability of reducing dietary intake of cholesterol and of reducing the amount of the more saturated fats and replacing them with polyunsaturated fats. The resulting dried egg product from which the free cholesterol has been virtually eliminated is considered desirable in the nutrition of persons with cardiovascular disease problems. Consequently, Canadian Pat. Nos. 898,056 issued Apr. 18, 1972 to Corn Products Company and 903,552 issued June 27, 1972 to CPC International Inc. provide procedures for removing cholesterol by extracting dried egg yolk solids with a non-polar solvent, e.g., n-hexane, to remove the readily extractable cholesterol.

A major deficiency of this procedure is that the defatted egg yolk material may contain 150 ppm or more of a residual solvent. Such n-hexane solvent is not a desirable constituent of a food product and hence the defatted egg yolk material is not optimally edible.

SUMMARY OF THE INVENTION

(i) Aims of the Invention

Accordingly, it is an object of this invention to provide a procedure for providing free cholesterol from egg yolk products.

Another object of this invention is to provide a process for providing an edible dried egg product from which the cholesterol has been virtually eliminated.

Yet another object of this invention is to provide a process for the production of by-products from egg yolks which may be utilized in soap production.

(ii) Statements of Invention

Thus, by this invention, a process is provided which comprises: (a)Ii) contacting a dried egg powder with an aqueous ethanol solution, (ii) providing an edible solid egg material from which a substantial portion of the free cholesterol has been removed and an aqueous ethanolic solution containing egg fats and cholesterol, and (iii) recovering such solid; (b) (i) subjecting such aqueous ethanolic solution to a saponification in order to provide a free cholesterol-containing solution and a saponified fatty acid, and (ii) recovering such fatty acid; and (c) (i) concentrating the cholesterol-containing solution in a hydrocarbon solbent, and (ii) thereafter recovering crystallized free cholesterol from solution in the hydrocarbon solvent. Thus, it is seen that three products are recovered; substantially cholesterol-free edible egg powder; fatty acid; and free cholesterol.

(iii) Other Features of the Invention

In one feature, the dried egg powder is whole egg powder, while in another feature, the egg powder is powdered egg yolk.

In a preferred feature, the aqueous ethanol solution is aqueous 95% ethanol.

In still another feature, the saponification is carried out by heating in an aqueous ethanolic solution of potassium hydroxide.

In yet another feature, the saponified fatty acid is recovered as a fatty acid salt.

In still another feature, the solution containing the cholesterol and the saponified fatty acid is treated with a salt, a hydrocarbon solvent and an aqueous ethanolic solution, whereby such cholesterol is removed in solution in the organic solvent, and whereby such fatty acid is recovered as a fatty acid salt precipitate.

In yet another feature, the saponified cholesterol solution is extracted with petroleum ether.

In a further feature, the cholesterol is purified with methanol.

Thus, the present invention provides processes for the extraction of free crystalline cholesterol ($C_{27}H_{46}O$) from products related to whole eggs, such as, dried whole egg or dried egg yolk.

BRIEF DESCRIPTION OF THE DRAWINGS

The accompanying drawing is a schematic flow sheet of the procedure of one embodiment of the invention.

DETAILED DESCRIPTION OF THE DRAWING

As seen in the flow sheet, the egg powder 10, either egg yolk powder or whole egg powder, is mixed with 95% ethanol at 11 and filtered at 12 to provide a solid material 13 and a filtrate 14.

Solid 13 is mixed with 95% ethanol at 15 and is then filtered to provide dry egg powder 16 and a filtrate which is added to filtrate 14.

The ethanol was removed from the filtrate 14 by reduced pressure at 17 to provide a residue 18. The residue was mixed with 95% ethanol at 19, KOH at 20 and water at 21 and heated for 2 hours at 60°–70° C. to provide a solution 22.

Solution 22 is cooled to provide solution 23 which is extracted with NaCl at 24, petroleum ether at 25 and ethanol at 26 and stirred. Upon settling, it provided a three-phase solution 27. The lower phases 28 were again extracted with petroleum ether at 29 and the upper phase added to the first upper phase 30 to provide a combined petroleum ether phase 31. The lower phases 32 provided fatty acid salts 33. The solvent was removed from the combined petroleum ether phases 31 by heating under reduced pressure and free cholesterol 34 was removed.

DESCRIPTION OF EXAMPLES OF PREFERRED EMBODIMENTS

The following are examples of this invention.

EXAMPLE I

Extraction of Whole Egg Powder (a) Egg powder (50 g) was combined with 95% ethanol (600 ml) and the mixture was stirred at room temperature (25–30° C.) for 2 hours. The mixture was filtered and the egg powder was washed with more 95% ethanol to give a filtrate of 600 ml and egg solid which on drying in air weighed 35 g. A portion of the filtrate (10%) was taken for analysis.

The solvent was removed from the remaining filtrate under reduced pressure. The remaining residue was combined with 95% ethanol (65 ml), potassium hydroxide (45 g) and water (65 ml) and the resulting mixture was stirred at 60°–70° C. for 2 hours. The solution was cooled and 5% sodium chloride solution (330 ml), petroleum ether, bp 60°–80° (700 ml) and 95% ethanol (150 ml) were added and the mixture was stirred for 2–3 minutes. On settling three layers were apparent. The lower two were separated and the petroleum ether layer was collected. The bottom two layers were extracted with petroleum ether (3 times with 200 ml) and the extracts were combined to give a final extract of 1400 ml. The combined extracts were dried ($MgSO_4$) and filtered. A known fraction of the total filtrate was used for analysis.

The solvent was removed from the remainder of the extract to give a yellowish solid residue which was recrystallized from methanol to give white needles. Two crops were usually recovered.

The results are summarized below in Table II.

(b) Dried whole egg (50 g) was stirred with 95% ethanol (300 ml) at room temperature for 4 hours. The mixture was filtered and the egg powder was washed with two 50 ml portions of 95% ethanol. A sample of the filtrate was taken for analysis and the solvent was removed from the remaining filtrate. The resulting oily residue was combined with 95% ethanol (25 ml), potassium hydroxide (28 g), and water (40 ml) and the mixture was stirred at 60°–70° C. for 2 hours.

On cooling, 5% aqueous sodium chloride (1000 ml), petroleum ether bp 60°–80° C. (300 ml), and 95% ethanol (50 ml) were combined, the petroleum ether layer being at the top. The two top layers were collected and these were then separated. The aqueous layer was further extracted with portions of petroleum ether (2 × 200 ml) and the combined petroleum ether extracts were dried ($MgSO_4$), then filtered, and a sample was removed for analysis. The solvent was removed from the rest of the petroleum ether extract and the residue remaining was recrystallized from methanol.

The middle layer of the extraction was reduced in volume and an oily residue resulted. Attempted crystallization from methanol gave no crystals but after evaporation of the methanol a soapy jelly-like material remained from which no cholesterol was obtained.

The results are summarized in Table II.

EXAMPLE II

Extraction of Powdered Yolk (a) Dry egg yolk (50 g) was stirred at room temperature with 95% ethanol (600 ml) for 2 hours. The mixture was filtered and the solid was washed with ethanol giving 700 ml of extract and 36 g of remaining egg yolk solid. A sample of the extract was removed for analysis.

The solvent was removed under vacuum from the remainder of the extract. The residue was hydrolysed while stirring for 2 hours at 60°–70° C. with 95% ethanol (40 ml), potassium hydroxide (45 g), and water (65 ml). The mixture was cooled and 5% aqueous sodium chloride (330 ml) and petroleum ether bp 60°–80° C. (700 ml) was added and the mixture was stirred for 2–3 minutes. Of the three layers the upper petroleum ether layer was collected. The other two layers were extracted with portions of petroleum ether (3 × 200 ml). The petroleum ether extracts were combined and dried ($MgSO_4$) and a sample was taken for analysis. The solvent was removed from the remaining extracts and the solid residue was recrystallized from methanol to give white needles in the first crop and yellowish needles in the second crop.

The results are summarized in Table II.

(b) Egg yolk powder (50 g) was stirred at room temperature with 95% ethanol (300 ml) for 4 hours. The mixture was filtered and the egg powder washed with some 95% ethanol. A sample of the extract was taken for analysis.

The solvent was removed from the remaining extract and the residue was heated for 2 hours at 60°–70° C. with 95% ethanol (25 ml), potassium hydroxide (28 g) and water (40 ml). On cooling, 5% aqueous sodium chloride (350 ml) and petroleum ether bp 60°–80° C. (300 ml) were added and the mixture was shaken. Three layers separated out and the upper two were collected. Ethanol (25 ml) was added to the two upper layers to effect clear separation and the two layers were separated and retained. The aqueous layer was extracted again with portions of petroleum ether bp 60°-80° C. (2 × 200 ml) and the upper two layers were retained and separated. The petroleum ether layer was dried (MgSO$_4$) and filtered and a sample was retained for analysis. The solvent was removed from the remainder of the layer and the solid residue was recrystallized from methanol to give white needles.

The middle layer was extracted with portions of petroleum ether (2 × 100 ml) and the extracts were treated as above and analyzed for cholesterol.

The results are summarized in Table II.

EXAMPLE III

Re-extraction of the aqueous layer

For one of the extractions (row a, Table II) the remaining aqueous layer was extracted further to determine whether more cholesterol could be removed. The aqueous layer was further extracted with portions of petroleum ether (2 × 100 ml). The two portions were combined and dried (MgSO$_4$). After filtering, the solvent was removed, the residue was dissolved, in ethyl acetate to give a 10 ml solution and analysis was carried out.

Test A — Mass spectra of crystalline cholesterol

Mass spectra of samples of cholesterol isolated in experiments a and e (Table II) were identical in fragmentation pattern to the mass spectrum of the standard sample from a commercial source that had been recrystallized twice from methanol/water and once from methanol.

Test B — Analysis for cholesterol

Analysis was carried out by means of gas liquid chromatography with stigmasterol being used as a standard. The stigmasterol ($C_{29}H_{48}O$) was a commercial sample and was recrystallized three times from 1,2-dichloroethane (m.p. 170°-172° C.; Lit 170° C.). The cholesterol used for the standardization curve was also a commercial sample which had been recrystallized twice from methanol/water and once from methanol (m.p. 148°-149° C.; Lit 148.5° C.).

A Varian 2700 flame ionization chromatograph with an OV 101 column under appropriate conditions gave a good convenient separation of the peaks corresponding to cholesterol and stigmasterol. A standard plot of mass ratios vs area ratios was produced using standard solutions of cholesterol and stigmasterol in ethyl acetate. Cholesterol concentrations in unknown samples were determined by combining known quantities of these solutions with known quantities of standard stigmasterol solutions. Peak area data were analyzed in the usual way.

Test C — Freeze drying of eggs

Freeze drying of 12 egg yolks and whole eggs gave information concerning the average mass of a wet large egg and a dry large egg and the yolks. The values obtained for one egg are:

mass of whole egg before drying — 49.65 g
mass of whole egg after drying — 13.26 g
mass of egg yolk before drying — 18.76 g
mass of egg yolk after drying — 8.56 g These values enabled rough comparison between different values for cholesterol content as quoted in the literature using a variety of units.

The Table II below provides an analysis of extracts from whole egg and egg yolk powder (cholesterol in 100 g of wet yolk; in parenthesis units are g/50 g of whole egg or egg yolk powder). The results in Example I(a) are shown in rows a and b in Table II which give typical values for analysis of cholesterol in the appropriate extracts before and after saponification, as well as amounts of cholesterol recovered in crystalline form. The results in Example I(b) are shown in row c in Table II which gives analytical data for extraction before and after saponification as well as the amount of cholesterol recovered in crystalline form. The results in Example II(a) are given in rows d and e in Table II which shows values for cholesterol analysis and recovery. The analysis and crystal recovery values in Example II(b) for cholesterol are given in row f of Table II.

TABLE II

| Example | | Powdered Egg Product | Cholesterol by Analysis before saponification | Cholesterol by Analysis after saponification | Crystal Recovery Mass | Crystal Recovery Crop | mp-° C (lit. 148.5) |
|---|---|---|---|---|---|---|---|
| I(a) | a | whole | 960mg (0.68g) +19mg[1] (0.013g) | 790mg (0.56g) +35mg[2] (0.025g) | 730mg (0.52g) 60mg (0.04g) | 1 2 | 147-149 |
| | b | whole | 1080mg (0.74g) | 1000mg (0.69g) | 770mg (0.53g) | 1 | 148-149 |
| I(b) | c[3] | whole | 800mg (0.6g) | 800mg (0.6g) | 400mg (0.3g) 400mg (0.3g) | 1 2 | 146.5-147 130 |
| II(a) | d | yolk | 980mg (1.07g) +62mg[1] (0.068g) | 980mg (1.07g) | 580mg (0.64g) 250mg (0.27g) | 1 2 | 149-150 140-145 |
| | e | yolk | 960mg (1.05g) | 990mg (1.08g) | 880mg (0.96g) | 1 | 147-148 |
| II(b) | f[3] | yolk | 900mg (.075g) | 600mg (0.62g) +133mg[4] (0.15g) | 450mg (0.49g) 50mg (0.05g) | 1 2 | 147-148.5 147-148 |

[1]Cholesterol extracted on re-extraction of egg powder
[2]Cholesterol extracted on re-extraction of the aqueous layer after saponification
[3]In general lower amounts of solvents and reagents were used for extraction and saponification
[4]Cholesterol from extraction of the middle layer The results in the above table show clearly the efficiency of the cholesterol extraction process of an aspect of this invention, and the purity of the cholesterol extracted.

Experiment D — Use of the low cholesterol egg powder in baking

The egg powder collected after extraction was stored in screw top bottles in a refrigerator.

The powder collected from one of the extractions of cholesterol from whole egg was used to prepare a raisin scone (recipe below) which was also prepared under similar conditions from fresh whole eggs. Eleven people were asked to sample the scones from the two different batches and to give their preference without knowledge of which one was made from the low cholesterol egg. Five of the people found no difference, three preferred the low cholesterol scone, and three preferred the fresh egg scone.

| Recipe | |
|---|---|
| Raisin Scones | |
| 3 c flour | ¼ c margarine |
| ¾ tsp salt | ¼ c shortening |
| 1 tsp baking powder | 1 c raisins |
| ¾ c sugar | 1 egg beaten (or whole egg powder + water equivalent*) |
| | milk |

Sift flour, salt, baking powder, sugar into mixing bowl. Cut in margarine and shortening. Add raisins. To beaten eggs, add enough milk to make 1 cup. Add milk mixture to flour mixture. Stir slightly to make a soft dough. Pat out to ½" thickness on a flour covered board. Cut and place on greased baking sheet. Bake at 425° F. for 15 minutes.

*The equivalent to one egg was taken to be approximately 13 g (2 tablespoons) of whole egg powder that was reduced in cholesterol +15 ml (1.5 fluid ounces) of water. This equivalence was roughly based on the quoted values for commercial whole egg of 9 eggs equivalent to 0.25 lb of whole egg powder +0.75 lb water.

SUMMARY

In summary, in carrying out the process, while the preferred aqueous ethanol solution is aqueous 95% ethanol, it is, of course, possible to use a more dilute solution. However, in such case, there would be more filtrate to be evaporated under reduced pressure by heating, at temperatures below 80° C at pressures of the order of 100 mm mercury. The suspending of the egg powder in the ethanol is generally carried out at room temperature. The amount of such aqueous ethanol solution used is variable but should be sufficient to dissolve the egg fats and the cholesterol. The non-soluble solid egg material may be recovered by any suitable manner, e.g., filtration, decantation, centrifugation, etc.

The liquid material, i.e., the aqueous ethanolic solution is dried to residue by heating, e.g. at temperatures below 80° C under reduced pressure, i.e., of the order of 100 mm mercury. The lower the pressure, the lower the evaporation temperature.

The saponification is generally carried out with an alkali metal hydroxide with heating, preferably at 60°-70° C for up to 2 hours with potassium hydroxide solution. The saponified solution is cooled to room temperature.

The cholesterol is separated from the fatty acid by the use of an organic nonpolar solvent for cholesterol. One example of such solvent is petroleum ether but other nonpolar solvents for cholesterol may be used, e.g., light naphtha, ligroin, etc. The cholesterol is recovered from solution in the usual way, e.g., by the use of heating at sub-atmospheric pressure, e.g., 100 mm of mercury.

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

We claim:

1. A process for separating and recovering discrete portions from egg which comprises the steps of:
   (A) extracting a dried egg powder with an aqueous ethanol solution under mild extraction conditions at a temperature of about 25°-30° C. for a time of from 2-4 hours, thereby providing:
      (i) an edible egg solid material from which at least about 70% by weight of cholesterol contained in the egg has been removed, and
      (ii) an aqueous ethanolic solution containing egg fats and free cholesterol;
   (B) recovering said edible egg solid (A) (i);
   (C) subjecting the egg fats and the cholesterol contained in said aqueous ethanolic solution (A) (i) to a saponification reaction, thereby to provide
      (iii) a free cholesterol-containing solution, and
      (iv) a saponified fatty acid;
   (D) extracting said saponified solution with an extractant including an organic non-polar solvent to form at least a two-phase solution;
   (E) recovering saponified fatty acid (D) (iv) from an upper phase of said solution;
   (F) concentrating said free cholesterol-containing solution in a lower phase of said solution; and
   (G) recovering free crystallized cholesterol from said solution in said organic non-polar solvent.

2. The process of claim 1 wherein the dried egg powder is whole egg powder.

3. The process of claim 1 wherein the dried egg powder is powdered egg yolk.

4. The process of claim 1 wherein the aqueous ethanol solution is aqueous 95% ethanol.

5. The process of claim 4 wherein the saponification is carried out by heating in an aqueous ethanolic solution of potassium hydroxide.

6. The process of claim 1 wherein the saponified fatty acid is recovered as a fatty acid salt.

7. The process of claim 6 wherein the solution containing the free cholesterol and the saponified fatty acid is treated with a salt, a hydrocarbon solvent and an aqueous ethanolic solution, whereby said free cholesterol is removed in solution in said organic solvent, and whereby said fatty acid is recovered as a fatty acid said precipitate.

8. The process of claim 7 wherein the hydrocarbon solvent is petroleum ether.

9. The process of claim 5 wherein the saponified cholesterol solution is extracted with petroleum ether.

10. The process of claim 6 wherein the cholesterol is purified with methanol.

11. A process for separating and recovering distinct portions from egg which comprises:
   (A) extracting dried egg powder with an aqueous ethanol solution, containing 95% ethanol under mild extraction conditions at a temperature of about 25°-30° C. for about 2-4 hours, thereby providing:
      (i) an edible egg solid material from which at least about 72% of cholesterol contained in the egg has been removed, and
      (ii) an aqueous ethanolic solution containing egg fats and free cholesterol;
   (B) recovering said edible egg solid (A) (i);
   (C) subjecting said aqueous ethanolic solution (A) (ii) to a saponification, thereby to provide (iii) a free cholesterol-containing solution, and
      (iv) a saponfied fatty acid;
   (D) extracting said saponified solution with an extractant comprising an organic non-polar solvent-/aqueous ethanol/aqueous salt solution to form a three-phase solution;
   (E) recovering said saponified fatty acid (C) (iv) in the upper two of said three-phase solution;
   (F) concentrating said free cholesterol-containing solution in said organic non-polar solvent; and
   (G) recovering free crystallized cholesterol from said solution in said organic solvent.

* * * * *